United States Patent [19]

Owen et al.

[11] Patent Number: 4,891,457

[45] Date of Patent: Jan. 2, 1990

[54] MULTISTAGE PROCESS FOR CONVERTING OLEFINS TO HEAVIER HYDROCARBONS

[76] Inventors: Hartley Owen, 5 Riverview Ter., Belle Mead, N.J. 08502; Bernard S. Wright, 13 Shagbark Ln., East Windsor, both of N.J. 08520

[21] Appl. No.: 775,907

[22] Filed: Sep. 13, 1985

[51] Int. Cl.$^4$ .............................................. C07C 2/12
[52] U.S. Cl. ................................... 585/312; 585/313; 585/314; 585/315; 585/322; 585/412; 585/415; 585/533
[58] Field of Search ............... 585/312, 313, 314, 315, 585/322, 412, 415, 417, 533

[56] References Cited

U.S. PATENT DOCUMENTS

| | | | |
|---|---|---|---|
| 3,827,968 | 1/1973 | Givens et al. | 585/415 |
| 4,150,062 | 4/1979 | Garwood et al. | 585/415 |
| 4,211,640 | 7/1980 | Garwood et al. | 585/415 |
| 4,433,185 | 2/1984 | Tabak | 585/312 |
| 4,444,988 | 4/1984 | Capsuto et al. | 585/415 |
| 4,465,884 | 8/1984 | Degnan et al. | 585/415 |
| 4,504,693 | 3/1985 | Tabak et al. | 585/520 |
| 4,517,396 | 5/1985 | Heck et al. | 585/415 |
| 4,542,247 | 9/1985 | Chang et al. | 585/254 |
| 4,608,450 | 8/1986 | Miller | 585/533 |

Primary Examiner—Asok Pal
Attorney, Agent, or Firm—Alexander J. McKillop; Charles J. Speciale; Lowell G. Wise

[57] ABSTRACT

A staged reactor technique for converting ethene-rich olefinic feedstock to heavier hydrocarbons, particularly gasoline and distillate range products. By employing low temperature and high temperature separators, an economic recycle is provided for each stage.

8 Claims, 1 Drawing Sheet

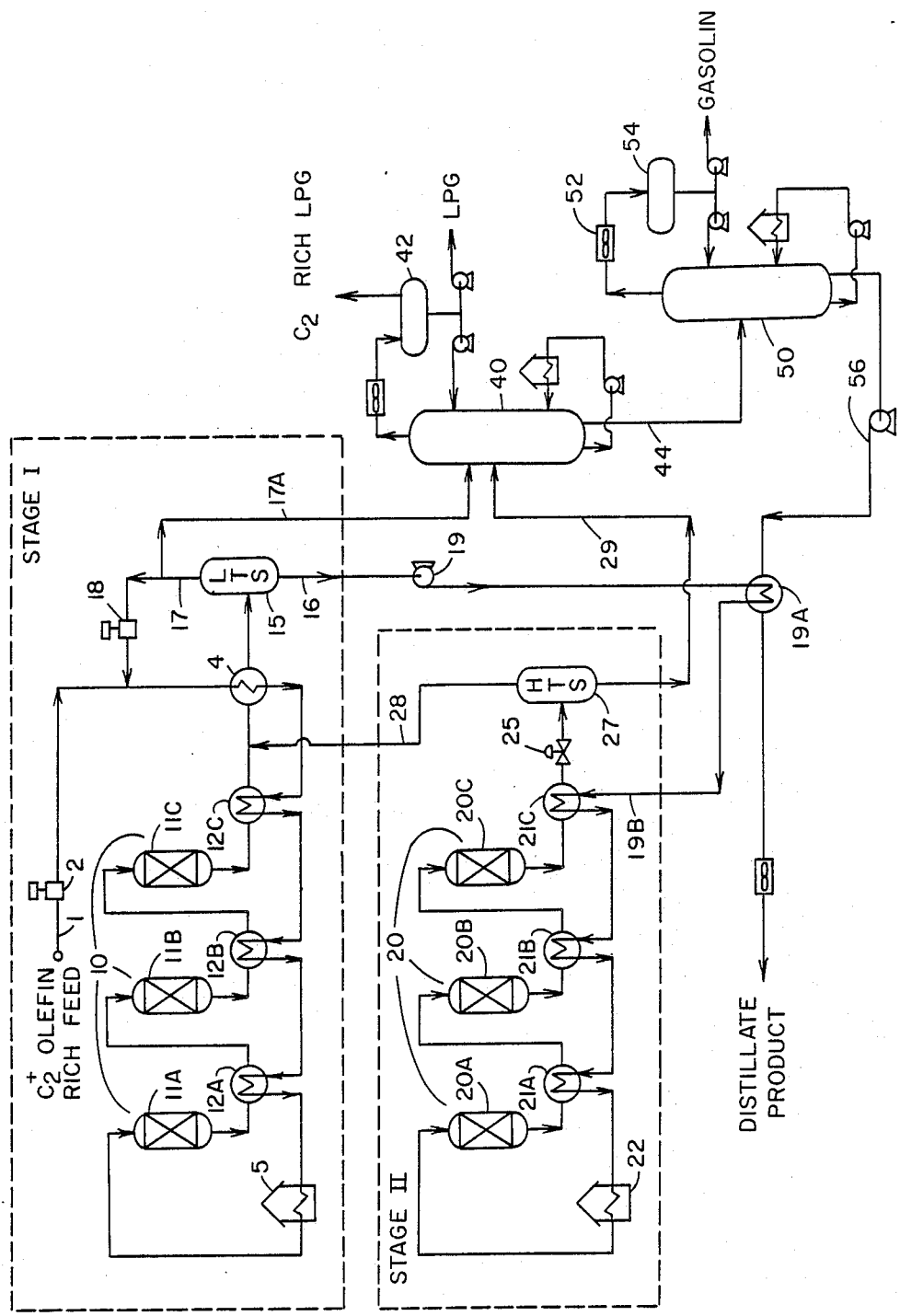

MULTISTAGE PROCESS FOR CONVERTING OLEFINS TO HEAVIER HYDROCARBONS

FIELD OF THE INVENTION

This invention relates to a system for upgrading light olefins to liquid hydrocarbons. In particular it provides a continuous process for producing distillate range fuel products by oligomerizing ethene-rich olefinic feedstock to produce a major amount of distillate product for use as diesel fuel or the like.

BACKGROUND OF THE INVENTION

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline can be produced in good yield by the MOGD process and may be recovered as a product or fed to a low severity reactor system for further conversion to distillate-range products. Distillate mode operation can be employed to maximize production of $C_{10}+$ aliphatics by reacting the lower olefins at high pressure and moderate temperature. Operating details for typical MOGD units are disclosed in U.S. Pat. Nos. 4,456,779; 4,497,968 (Owen et al) and U.S. Pat. No. 4,433,185 (Tabak), incorporated herein by reference.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2-C_6$ alkenes may be converted selectively; however, the low severity distillate mode conditions do not convert a major fraction of ethene. While propene, butene-1 and others may be converted to the extent of 50 to 95% in the distillate mode, only about 10 to 30% of the ethylene component will be converted.

SUMMARY OF THE INVENTION

A continuous multi-stage catalytic technique has been found for converting ethene-rich lower olefinic feedstock to heavier liquid hydrocarbon product. Methods and apparatus are provided for contacting ethene-rich feedstock at elevated temperature and moderate pressure in a primary stage high severity reaction zone with shape selective medium pore zeolite oligomerization catalyst to convert at least a portion of the lower olefinic components to intermediate olefinic hydrocarbons. Means are provided for cooling primary stage oligomerization reaction effluent from the high severity reaction zone to condense at least a portion of the intermediate hydrocarbons, separating the cooled and partially condensed high severity reactor effluent stream in a primary phase separation zone into a light gas phase stream comprising unreacted light olefin and a condensed liquid intermediate hydrocarbon stream. By recycling a major portion of the primary gas stream to the primary stage reaction zone, unreacted ethene and other gases may be further converted or provide reaction diluent. By pressurizing and contacting the intermediate liquid stream from the primary stage with shape selective medium pore zeolite oligomerization catalyst in a secondary stage distillate mode catalytic reactor system at elevated temperature and high pressure, a heavier hydrocarbon effluent stream is produced comprising distillate and lighter hydrocarbons.

Recycle for the secondary stage is provided by flashing and cooling the secondary stage effluent stream for separation in a secondary phase separation zone to recover a distillate-rich product stream and a lighter hydrocarbon vapor stream comprising intermediate hydrocarbons and recycling at least a portion of the recovered secondary stage vapor stream for combining in the primary stage effluent prior to phase separation.

BRIEF DESCRIPTION OF THE DRAWINGS

The single figure is a process flow sheet depicting the invention.

DESCRIPTION OF PREFERRED EMBODIMENTS

Catalyst versatility permits the same zeolite to be used in both the high severity primary stage and distillate mode secondary oligomerization stage. While it is within the inventive concept to employ substantially different catalysts in these stages, it is advantageous to employ a standard ZSM-5 having a silica alumina molar ratio of 70:1.

The oligomerization catalysts preferred for use herein include the medium pore shape selective crystalline aluminosilicate zeolites having a silica to alumina ratio of at least 12, a constraint index of about 1 to 12 and acid cracking activity of about 50-200. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449, 4,076,979, 3,832,449, 4,076,842, 4,016,245 and 4,046,839, 4,414,423, 4,417,086 and 4,517,396. The disclosures of these patents are incorporated herein by reference. A suitable catalyst for each fixed bed operation consisting essentially of ZSM-5 zeolite with 35 wt. % alumina binder in the form of cyclindrical extrudates of about 1–5 mm diameter. These zeolites may be employed in their acid forms or ion exchanged with suitable metal cations, such as Ni, Co and/or other metals of Periodic Groups III to VIII. Other catalysts which may be employed for converting lower olefins include the borosilicate, ferrosilicate, "silicalite" and/or synthetic mordenite materials.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

The preferred feedstock comprises at least about 15 mole ethene and may consist essentially of $C_2$–$C_6$ olefins, such normal mono-olefins and isomers thereof.

Stage I-High Severity Reactor Operation

The term high severity, as employed herein, refers to the combination of materials and conditions effective to convert a major amount (more than 50%) of ethene. This degree of reaction severity may be achieved by elevated temperature, catalyst activity, etc. in a known manner. In the drawing, ethene-rich olefinic feedstock is supplied to the plant through fluid conduit 1 under steady stream conditions. This $C_2$+ feedstream is pressurized by compressor 2 and then sequentially heated by passing through process heat exchange units 4, 12 and furnace 5 to achieve the temperature for catalytic conversion in reactor system 10, including plural reactor vessels 11A, B, C. The reactor sub-system section shown consists of three downflow fixed bed, series reactors on line with heat exchanger cooling means 12 A, B, C between reactors and following the subsystem. The reactor configuration allows for any reactor to be in any position, A, B or C. The reactor in position A has the most aged catalyst and the reactor in position C has freshly regenerated catalyst. The cooled reactor effluent from exchanger 4 is first separated in a primary phase low temperature separator unit (LTS) 15 is to provide a condensed $C_5$+ rich hydrocarbon liquid stream 16 and a primary light gas stream 17 comprising $C_2$–$C_4$ aliphatic hydrocarbons, along with ethene or other unreacted gaseous components which might be present in the feedstock, such as hydrogen, carbon oxides, methane, nitrogen or other inert gases. A major portion of this light gas stream is repressurized by compressor unit 18 for recycle with fresh feedstock from compressor 2.

A typical high severity multi-zone reactor system employs inter-zone cooling, whereby the reaction exotherm can be carefully controlled to prevent excessive temperature above the normal moderate range of about 260° to 370° C.

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a liquid stream to vaporize liquid hydrocarbons. Optional heat exchangers may recover heat from the effluent stream prior to fractionation. It is preferred to operate the high severity reactors at moderate pressure of about 1500 to 2900 kPa (200–400 psig), with a minimum olefin partial pressure of about 1200 kPa at the reactor system inlet.

The primary reactor system may contain multiple downflow adiabatic catalytic zones in each reactor vessel. The weight hourly space velocity (WHSV, based on total fresh feedstock) is about 0.1-2 LHSV. In this mode the molar recycle ratio for light gas is at least equimolar, based on total olefins in the fresh feedstock. The preferred molar ratio of recycle to fresh feedstock olefin is at least 2:1.

Stage II - Distillate Mode Oligomerization Reactor Operation

The secondary distillate production stage provides catalytic oligomerization reactor means containing medium pore shape selective zeolite oligomerization catalyst for converting lower and intermediate range olefinic hydrocarbons from the Stage I to liquid hydrocarbons comprising a major amount of distillate. Process stream 16, preferably comprising at least 75 mole % $C_5$ to $C_9$ aliphatic hydrocarbons, is pressurized for a substantially different process condition by pump means 19, operatively connected to provide a fluid handling system between Stages I and II. The intermediate liquid stream is preheated by indirect heat exchange with distillate product in exchanger 19A and passed to the Stage II subsystem at a pressure of at least about 4000 kPa, preferably about 4225 to 7000 kPa (600 to 1000 psig).

A typical distillate mode secondary stage reactor system 20 is depicted. A plural reactor system may be employed with inter-reactor cooling, whereby the reaction exotherm can be carefully controlled to prevent excessive temperature above the normal moderate range of about 190° to 315° (375°-600° F.). The olefinic intermediate stream comprising the $C_5$+ hydrocarbons is introduced through conduit 19B and carried by a series of conduits through heat exchangers 21A, B, C and furnace 22 where the intermediate stream is heated to reaction temperature. The olefinic stream is then carried sequentially through a series of zeolite beds 20A, B, C wherein a major portion of the olefin content is converted to heavier distilate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 21A and 21B provide inter-reactor cooling and 21C further reduces the effluent. After flashing by means of pressure reduction valve 25, the Stage II effluent is passed to secondary high temperature phase separator means 27.

This HTS unit is operated in a manner to recover the major amount of $C_{10}$+ hydrocarbons, while vaporizing light and intermediate ($C_9$−) hydrocarbons at a pressure below 4000 kPa and temperature at least 100° C. higher than LTS unit 15. This secondary vapor stream is recycled to Stage I via conduit 28. Advantageously, the HTS unit is operated at a pressure slightly above the Stage I effluent stream (e.g. about 3000 to 3500 kPa), with a recycle control system to maintain the desired pressure and flow rates.

Preferably, the secondary stage reactor conditions are optimized to produce heavy liquid hydrocarbons having a normal boiling above 165° C. (330° F.). A typical secondary stage HZSM-5 fixed bed reactor system may be operated at about 0.5 to 2 liquid hourly space velocity (based on total olefins fed to reactors), temperature of 230° C. (450° F.) (SOC) to 315° C. (600° F.) (EOC) and a total pressure of 4225 kPa (600 psiq), with a minimum olefin partial pressure at the inlet of about 1100 kPa (160 psig).

Product fractionation is achieved outside the recycle loops by passing a gas phase slip stream 17A and distillate-rich liquid stream 29 to a debutanizer tower 40 where $C_3$–$C_4$ LPG product is recovered from overhead condenser separator 42 and $C_2^-$ of gas containing some unreacted ethene and a small amount of $C_4^-$ hydrocarbons is recovered. The $C_5^+$ liquid bottoms stream 44 is passed to product splitter tower 50 where $C_5$–$C_9$ raw gasoline product is recovered from the overhead condenser 52 and accumulator 54 and the raw distillate product is recovered as a $C_{10}^+$ bottoms stream via conduit 56 and exchanger 19A. Typical product fractionation systems are described in U.S. Pat. Nos. 4,456,779 and 4,504,693 (Owen et al).

It is within the inventive concept to cascade a major amount of $C_5^+$ hydrocarbons from the primary stage into the distillate mode reactor. This will optimize the process and will maximize distillate production by polymerizing gasoline boiling range components. Because the primary stage is operated at a pressure level of about 200-400 psig ($\sim$1500-2900 kPa), the compression requirements are efficient. Also, common separators are employed for both stages to effect preliminary product separation and provide recycle economically. In the prior art, a deethanizer and debutanizer is used to supply LPG recycle to one or both stages. Usually prior product fractionation is within the recycle loop for both stages, whereas in the present process the product fraction is outside the recycle loop. Consequently the new process will have both a lower capital investment and operating cost than that for prior systems.

While the invention has been described by specific examples and embodiments, there is no intent to limit the inventive concept except as set forth in the following claims.

We claim:

1. A continuous multi-stage catalytic process for converting ethene-rich lower olefinic feedstock to heavier liquid hydrocarbon product, comprising the steps of
   contacting ethene-rich feedstock at elevated temperature and moderate pressure in a primary stage high severity reaction zone with shape selective medium pore zeolite oligomerization catalyst to convert at least a portion of the lower olefinic components to intermediate olefinic hydrocarbons;
   cooling primary stage oligomerization reaction effluent from the high severity reaction zone to condense at least a portion of the intermediate hydrocarbons, separating the cooled and partially condensed high severity reactor effluent stream in a primary phase separation zone into a light gas phase stream comprising unreacted light olefin and a condensed liquid intermediate hydrocarbon stream;
   recycling a major portion of the primary gas stream to the primary stage reaction zone;
   pressurizing and contacting the intermediate liquid stream from the primary stage with shape selective medium pore zeolite oligomerization catalyst in a secondary stage distillate mode catalytic reactor system at elevated temperature and high pressure to provide a heavier hydrocarbon effluent stream comprising distillate and lighter hydrocarbons;
   flashing and cooling the secondary stage effluent stream for separating in a secondary phase separation zone to recover a distillate-rich product stream and a lighter hydrocarbon vapor stream comprising intermediate hydrocarbons, wherein the secondary phase separation zone is maintained at operating pressure between the primary and secondary stage reactors and wherein the temperature of said secondary separation zone is maintained higher than said primary separation zone to vaporize a major amount of the $C_9^-$ hydrocarbons in the secondary stage effluent; and
   recycling at least a portion of the recovered secondary stage vapor stream for combining in the primary stage effluent prior to phase separation.

2. The process of claim 1 wherein a major amount of $C_5^+$ intermediate hydrocarbons present in the primary stage effluent is condensed and further converted in the secondary stage.

3. The process of claim 2 wherein the liquid intermediate stream comprises at least 75 mole % $C_5$ to $C_9$ aliphatic hydrocarbons.

4. The process of claim 1 wherein the feedstock comprises at least about 15 mole % ethene.

5. The process of claim 4 wherein the feedstock consists essentially of $C_2$–$C_6$ olefins.

6. The process of claim 1 wherein the catalyst in both stages comprises ZSM-5.

7. The process of claim 1 wherein a gas slipstream comprising $C_4^-$ light gas is removed from the primary stage separator and recovered therefrom.

8. In a continuous multi-stage catalytic process for converting ethene-rich olefinic feedstock to heavier liquid hydrocarbon product, comprising the steps of
   contacting ethene-rich feedstock at elevated temperature and moderate pressure up to about 2900 kPa in a primary stage high severity reaction zone with shape selective medium pore zeolite oligomerization catalyst to convert at least a portion of the lower olefinic components to intermediate olefinic hydrocarbons;
   cooling primary stage oligomerization reaction effluent from the high severity reaction zone to condense at least a portion of the intermediate hydrocarbons, separating the cooled and partially condensed high severity reactor effluent stream in a primary phase separation zone into a light gas phase stream comprising unreacted light olefin and a condensed liquid intermediate hydrocarbon stream;
   recycling a major portion of the primary gas stream to the primary stage reaction zone;
   pressurizing and contacting the intermediate hydrocarbon stream from the primary stage with shape selective medium pore zeolite oligomerization catalyst in a secondary stage distillate mode catalytic reactor system at elevated temperature and process pressure of at least 4000 kPa to provide a heavier hydrocarbon effluent stream comprising distillate and lighter hydrocarbons, the improvement which comprises:
   flashing and cooling the secondary stage effluent stream at a pressure of about 3000 to 3500 kPa for separation in a secondary phase separation zone to recover a distillate-rich product stream and a lighter hydrocarbon vapor stream comprising $C_5$–$C_9$ intermediate hydrocarbons;
   maintaining temperature of said secondary separation zone at least 100° C. higher than said primary separation zone to vaporize a major amount of the $C_9^-$ hydrocarbons in the secondary stage effluent; and
   recycling at least a portion of the recovered secondary stage vapor stream for combining in the primary stage effluent prior to phase separation.

* * * * *

UNITED STATES PATENT AND TRADEMARK OFFICE
CERTIFICATE OF CORRECTION

PATENT NO. : 4,891,457

DATED : January 2, 1990

INVENTOR(S) : Hartley Owen & Bernard S. Wright

It is certified that error appears in the above-identified patent and that said Letters Patent is hereby corrected as shown below:

On the title page, insert:
  --[73] Assignee: Mobil Oil Corporation--

Signed and Sealed this

Nineteenth Day of March, 1991

Attest:

HARRY F. MANBECK, JR.

Attesting Officer

Commissioner of Patents and Trademarks